United States Patent [19]

Shouldice

[11] Patent Number: 4,769,151
[45] Date of Patent: Sep. 6, 1988

[54] HEATER CONTROL FOR LIQUID FLOWING THROUGH A CHAMBER

[75] Inventor: David R. Shouldice, Lakewood, Colo.

[73] Assignee: Cobe Laboratories, Inc., Lakewood, Colo.

[21] Appl. No.: 925,886

[22] Filed: Oct. 30, 1986

[51] Int. Cl.$^4$ .............................................. B01D 13/00
[52] U.S. Cl. .................................... 210/646; 210/181
[58] Field of Search .................. 210/321.3, 96.2, 180, 210/181, 646; 219/501, 497

[56] References Cited

U.S. PATENT DOCUMENTS 3,878,095  4/1975  Frasier et al. .................. 210/180 X
4,093,847  6/1978  Walker et al. ...................... 219/501

FOREIGN PATENT DOCUMENTS 1512265  5/1978  United Kingdom .
2012613  8/1979  United Kingdom .
2052109  1/1981  United Kingdom .
2148467  5/1985  United Kingdom .

Primary Examiner—Frank Spear

[57] ABSTRACT

Fluid flow apparatus comprising a housing defining a chamber and having an inlet and outlet for liquid flowing into and out of the chamber, an electrically-powered heater located in the chamber, a temperature sensor mounted to sense temperature of liquid prior to entering the chamber and providing inlet temperature signals indicating inlet temperature, and a controller electrically connected to receive the inlet temperature signals from the temperature sensor and to control a duty cycle of the heater in response to the inlet temperature signals.

21 Claims, 1 Drawing Sheet

HEATER CONTROL FOR LIQUID FLOWING THROUGH A CHAMBER

FIELD OF THE INVENTION

The invention relates to controlling an electrical heater in a fluid flow chamber.

BACKGROUND OF THE INVENTION

Liquid flowing through a fluid flow chamber can be heated using an electrically-powered immersion heater that is alternatively switched on and off. Such heaters have been used in dialysate preparation apparatus to heat water used in making dialysate; a temperature sensor senses the temperature downstream of the heater, and the sensed temperature value is used to control the switching of the heater on and off.

SUMMARY OF THE INVENTION

I have discovered that a heater for liquid flowing through a chamber can be quickly and efficiently adjusted in response to changes in inlet temperature so as to avoid large variations in outlet temperature by sensing the inlet temperature of the liquid and using the sensed temperature in adjusting a duty cycle of the heater.

In preferred embodiments there also is a temperature sensor that senses the outlet temperature; the duty cycle is determined by multiplying a heater constant times the difference between a commanded outlet temperature and the inlet temperature; the heat constant is a function of the difference between the commanded outlet temperature and the sensed outlet temperature; and a final temperature sensor located downstream of a mixing chamber for mixing a second liquid with the heated liquid is used to compensate for temperature changes downstream of the heater.

Other advantages and features of the invention will be apparent from the following description of the preferred embodiment thereof and from the claims.

DESCRIPTION OF THE PREFERRED EMBODIMENT

Figure 1:
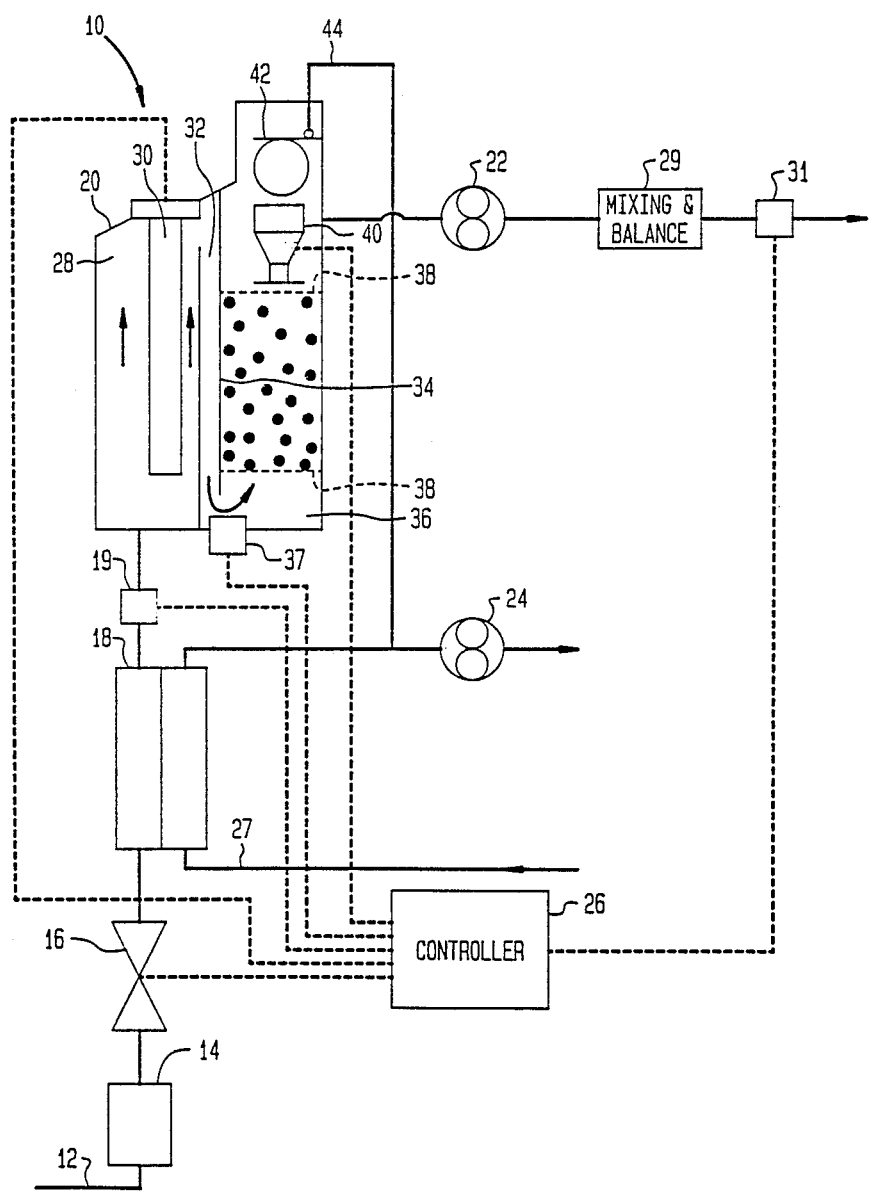

The preferred embodiment will now be described.

Drawing

The drawing is a diagrammatic representation of a portion of a dialysate preparation machine.

STRUCTURE

Referring to the drawing, there is shown apparatus 10 for deaerating water used in a dialysate preparation and supply machine of the type shown in Johnson U.S. Pat. No. 4,371,385. It includes inlet 12 for receiving tap water, inlet pressure regulator 14 (adjusted to have an outlet pressure of 6 psi when its outlet is not connected to a further pressure reducer), two-position (open-closed) solenoid valve 16, heat exchanger 18 (efficiently constructed so as to provide 80% of the heat needed to heat incoming water under operating conditions), inlet temperature sensor 19, heater/deaerator 20, deaeration pump 22, vacuum/waste pump 24, and electronic controller 26. Pumps 22, 24 are positive displacement gear pumps.

Downstream of dearation pump 22 are mixing chambers (in which dialysate concentrate is mixed with water), conductivity sensors (used to control the addition of concentrate), and balance chambers (to balance flow into and out of the dialyzer to control ultrafiltration), all of which are indicated by mixing and balance block 29 on the drawing. Downstream of these components is final temperature sensor 31, sensing the temperature of the combined water and concentrate flow just prior to entering the dialyzer. Inlet 27 of heat exchanger 18 is connected to receive spent dialysate from the balance chambers downstream of the dialyzer (not shown).

Heater/deaerator 20 includes tubular flow passage 28, which surrounds heater 30 (an 800-watt, electrically-powered immersion heater) and overflows into passage 32 on the left side of baffle 34 between the heating zone in passage 28 and dearation chamber 36. At the bottom of passage 32 is outlet temperature sensor 37. Deaeration chamber 36 includes polypropylene particles (spheres and cylinders approximately 0.090" in diameter) that are prevented from flowing beyond screens 38 located below level sensor 40. At the top of deaeration chamber 36 is bleed valve 42 blocking flow of liquid through gas outlet 44 connected to vacuum/waste pump 24.

Electronic controller 26 is connected to receive signals indicating temperature from temperature sensors 19, 31, 37, and to use these signals in controlling the duty cycle of heater 30. It is also connected to receive signals from level sensor 40 and to control valve 16 and to control other components (not shown) of the dialysate preparation machine.

Operation

Water entering from inlet 12 passes through pressure regulator 14, which provides protection from large line pressure variations, and solenoid valve 16, which is alternately opened and closed and has a 6-second period. The duty cycle of valve 16 is controlled by controller 26 so as to be open a portion of the 6-second period depending upon the liquid level indicated by the output voltage from level sensor 40.

Water flows through heat exchanger 18, receiving heat from the spent dialysate, and enters heating passage 28, flows upward in it, spills over into passage 32 and flows under baffle 34 into deaeration chamber 36. The liquid in heater/deaerator 20 is subjected to negative pressure by dearation pump 22 and by vacuum pump 24.

Heater 30 is alternately switched on and off a number of times each period of 256 line cycles, i.e., about every 4.27 seconds for 60 Hz alternating current. The duty cycle, D is determined by the following equation:

$$D = K_H \times (T_c - T_o)$$

where:

$T_c$ is the commanded temperature,
$T_o$ is the inlet temperature sensed by sensor 19, and
$K_H$ is the heater constant, given by the following equation:

$$K_H = \left[ K_p(T_c - T_l) + K_i \int_{to}^{ti} (T_c - T_l) + K_d\, d(T_c - T_l)/dt \right] \times Q/LV^2$$

where:

$T_1$ is the outlet temperature sensed by sensor 37, $K_p$, $K_i$, and $K_d$ are the gain values for the proportional, integral, and derivative terms of a PID control algorithm used to adjust for the error in actual outlet temperature according to procedures well known in the art, e.g., as disclosed in Kuo, *Digital Control Systems*, Holt, Rinehart & Winston, Inc., 1980, pp. 509–514, which is hereby incorporated by reference, $K_p$ and $K_i$ being empirically determined, and $K_d$ being set equal to zero in the preferred embodiment, LV is the line voltage for heater 30, and Q is the flow rate of water through the heater, which can be set to different values by the operator.

This calculation is performed after each sample, and the duty cycle value is some number of the 256 line cycles in each period divided by 256. By period of the duty cycle herein I mean the 4.27-second period.

The duty cycle is distributed throughout the 4.27-second period; e.g., a 50% duty cycle will cause the heater to be on every other cycle (of the 256 cycles in the period); a 25% duty cycle will cause the heater to be on every fourth cycle, and a duty cycle between these two would result in the heater being on, in addition to every fourth cycle, the appropriate number of additional cycles distributed throughout the 4.27-second period. Changes in duty cycle are immediately implemented in the control of the heater.

The integrated portion of the calculation is related to the long-term average, and the proportional portion is related to the actual temperature error. The use of the integrated portion avoids phase lag oscillation that might otherwise result from using the porportional portion of the calculation alone. The LV and Q terms adjust the heater constant term, $K_H$, in response to the effect of line voltage and flow rate, respectively. When starting up the dialysate apparatus, the integral term of the PID algorithm is preloaded to achieve an expected heater constant.

Pump 22 is operated at a fixed voltage to pump at a constant rate (the value of which can be adjusted by the operator), and pump 24 is operated to pull on the air in chamber 36 to maximize the vacuum in chamber 36, without overpowering pump 22. The negative pressure and increased temperature cause volatilization of dissolved gas from the liquid. Plastic particles between screens 38 provided nucleation sites at which air bubbles form. Gas accumulating above the liquid surface passes through valve 44 and pump 24 while average liquid level is maintained constant by level sensor 40.

Deaerated water supplied by pump 22 to the remainder of the hydraulic circuitry of the dialysate preparation machine is mixed with dialysate concentrate and provided to the dialysate side of a dialyzer. Particularly during a dialysate session, the final temperature sensed by final temperature sensor 31 is used to adjust the commanded temperature, $T_c$, if necessary, to account for downstream temperature changes, caused, e.g., by the addition of concentrate.

Spent dialysate returns from the dialyzer to inlet 27 of heat exchanger 18 and is removed via vacuum/waste pump 24. Because heat exchanger 18 provides 80% of the heat necessary to heat incoming water under normal operating conditions, there is a very significant increase in the inlet temperature, $t_o$, when the heated spent dialysate initially passes though the spent side of heat exchanger 18 after passing through the rest of the system. This substantial change in preheating very significantly decreases the heat to be supplied by heater 30. The use of the sensed inlet temperature permits controller 26 to very quickly adjust the duty cycle to add the amount of heat required to bring the preheated water to the desired commanded level and avoids the overshooting (and further oscillation around the commanded level) that would result from use of only outlet temperature.

Other Embodiments

Other embodiments of the invention are within the scope of the following claims.

What is claimed is:

1. Fluid flow apparatus comprising
    a housing defining a chamber and having an inlet and outlet for liquid flowing into and out of said chamber,
    an electrically-powered heater located in said chamber,
    a first temperature sensor mounted to sense temperature of liquid prior to being heated in said chamber, said first sensor providing preheat temperature signals indicating preheat temperature, and
    a controller electrically connected to receive said preheat temperature signals from said first temperature sensor and to control a duty cycle of said heater so as to be switched on and switched off during duty cycle periods, the proportion of time said heater being on during a said duty cycle period being adjusted in response to said preheat signals, said heater being turned on or off for integer line cycles, said period including a plurality of line cycles,
    said controller determining said duty cycle by multiplying a heater constant times the difference between a commanded outlet temperature and said preheat temperature.

2. The apparatus of claim 1 further comprising a second temperature sensor mounted to sense the temperature of liquid after it has left said chamber, said second sensor providing outlet temperature signals indicating outlet temperature, and wherein said controller is electrically connected to receive said outlet temperature signals from said second temperature sensor.

3. The apparatus of claim 1 wherein said heater constant is a function of the difference between said commanded outlet temperature and said outlet temperature.

4. The apparatus of claim 3 wherein said controller calculates the integral of said difference in setting said duty cycle.

5. The apparatus of claim 4 wherein said controller calculates the sum of a constant times said difference and a constant times said integral.

6. The method of using the apparatus of claim 1.

7. The apparatus of claim 1 further comprising a heat exchanger preheating liquid flowing from said inlet using heat of liquid that has flowed out of said chamber.

8. Fluid flow apparatus comprising
    a housing defining a chamber and having an inlet and outlet for liquid flowing into and out of said chamber,
    an electrically-powered heater located in said chamber,
    a first temperature sensor mounted to sense temperature of liquid prior to being heated in said chamber, said first sensor providing preheat temperature signals indicating preheat temperature, and
    a controller electrically connected to receive said preheat temperature signals from said first temperature sensor and to control a duty cycle of said heater so as to be switched on and switched off a plurality of times during each duty cycle period, the on and off conditions being distributed throughout said period, the proportion of time said heater being on during a said duty cycle period being adjusted in response to said preheat signals, said heater being turned on or off for integer line cycles, said period including a plurality of line cycles.

9. The apparatus of claim 8 wherein said controller calculates a desired duty cycle a plurality of times during each period of the duty cycle.

10. Fluid flow apparatus comprising a housing defining a chamber and having an inlet and outlet for liquid flowing into and out of said chamber, an electrically-powered heater located in said chamber, a first temperature sensor mounted to sense temperature of liquid prior to being heated in said chamber, said first sensor providing preheat temperature signals indicating preheat temperature, and a controller electrically connected to receive said preheat temperature signals from said first temperature sensor and to control a duty cycle of said heater so as to be switched on and switched off during duty cycle periods, the proportion of time said heater being on during said duty cycle period being adjusted in response to said preheat signals, said heater being turned on or off for integer line cycles, said period including a plurality of line cycles, a final temperature sensor downstream of a mixing chamber for mixing a second liquid with liquid from said outlet, said final temperature sensor providing final temperature signals, said controller receiving said final temperature signals and adjusting a commanded outlet temperature based on them.

11. Dialysate preparation apparatus comprising a housing defining a chamber and having an inlet and outlet for liquid flowing into and out of said chamber, a first temperature sensor mounted to sense temperature of liquid prior to being heated in said chamber, said first sensor providing preheat temperature signals indicating preheat temperature, and a controller electrically connected to receive said preheat temperature signals from said first temperature sensor and to control a duty cycle of said heater so as to be switched on and switched off during duty cycle periods, the proportion of time said heater being on during a said duty cycle period being adjusted in response to said preheat signals, said heater being turned on or off for integer line cycles, said period including a plurality of line cycles, a final temperature sensor downstream of a mixing chamber for mixing a second liquid with liquid from said output, said final temperature sensor providing final temperature signals, said controller receiving said final temperature signals and adjusting a command outlet temperature based on them.

12. Dialysate preparation apparatus comprising a housing defining a chamber and having an inlet and outlet for liquid flowing into and out of said chamber, an electrically-powered heater located in said chamber, a first temperature sensor mounted to sense temperature of liquid prior to being heated in said chamber, said first sensor providing preheat temperature signals indicating preheat temperature, and a controller electrically connected to receive said preheat temperature signals from said first temperature sensor and to control a duty cycle of said heater so as to be switched on and switched off during duty cycle periods, the proportion of time said heater being on during a said duty cycle being adjusted in response to said preheat signals, said heater being turned on or off for integer line cycles, said period including a plurality of line cycles, said controller determining said duty cycle by multiplying a heater constant times the difference between a commanded outlet temperature and said preheat temperature.

13. The method of using the apparatus of claim 12.

14. The apparatus of claim 12 further comprising a second temperature sensor mounted to sense the temperature of liquid after it has left said chamber, said second sensor providing outlet temperature signals indicating outlet temperature, and wherein said controller is electrically connected to receive said outlet temperature signals from said second temperature sensor.

15. The apparatus of claim 14 wherein said controller determines said duty cycle by multiplying a heater constant times the difference between a commanded outlet temperature and said inlet temperature.

16. The apparatus of claim 15 wherein said heater constant is a function of the difference between said commanded outlet temperature and said outlet temperature.

17. The apparatus of claim 16 wherein said controller calculates the integral of said difference in setting said duty cycle.

18. The apparatus of claim 17 wherein said controller calculates the sum of a constant times said difference and a constant times said integral.

19. The apparatus of claim 12 further comprising a heat exchanger preheating liquid flowing into said inlet using heat of liquid that has flowed out of said chamber.

20. Dialysate preparation apparatus comprising a housing defining a chamber and having an inlet and outlet for liquid flowing into and out of said chamber, an electrically-powered heater located in said chamber, a first temperature sensor mounted to sense temperature of liquid prior to being heated in said chamber, said first sensor providing preheat temperature signals indicating preheat temperature, and a controller electrically connected to receive said preheat temperature signals from said first temperature sensor and to control a duty cycle of said heater so as to be switched on and switched off a plurality of times during each duty cycle period, the on and off conditions being distributed throughout said period, the proportion of time said heater being on during a said duty cycle period being adjusted in response to said preheat signals, said heater being turned on or off for integer line cycles, said period including a plurality of line cycles.

21. The apparatus of claim 20 wherein said controller calculates a desired duty cycle a plurality of times during each period of the duty cycle.

* * * * *

UNITED STATES PATENT AND TRADEMARK OFFICE
CERTIFICATE OF CORRECTION

PATENT NO. : 4,769,151

DATED : September 6, 1988

INVENTOR(S) : David R. Shouldice

It is certified that error appears in the above-identified patent and that said Letters Patent is hereby corrected as shown below:

Column 1, line 31, "heat" should be --heater--;

Column 3, line 54, "Particularly" should be -- Periodically --.

Column 4, line 55, "from" should be --into--;

Signed and Sealed this

Eighteenth Day of July, 1989

Attest:

DONALD J. QUIGG

Attesting Officer

Commissioner of Patents and Trademarks